United States Patent
Herzinger et al.

(12) 
(10) Patent No.: US 6,455,853 B2
(45) Date of Patent: Sep. 24, 2002

(54) DETERMINATION OF THICKNESS AND IMPURITY PROFILES IN THIN MEMBRANES UTILIZING SPECTORSCOPIC DATA OBTAINED FROM ELLIPSOMETRIC INVESTIGATION OF BOTH FRONT AND BACK SURFACES

(75) Inventors: Craig M. Herzinger, Lincoln, NE (US); Thomas E. Tiwald, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 26 days.

(21) Appl. No.: 09/756,515

(22) Filed: Jan. 9, 2001

Related U.S. Application Data
(60) Provisional application No. 60/183,977, filed on Feb. 22, 2000.

(51) Int. Cl.$^7$ ................................................ G01N 21/21
(52) U.S. Cl. ............................... 250/341.4; 250/341.3; 250/341.8; 356/364; 356/369
(58) Field of Search .................... 250/339.07, 341.3, 250/341.8, 341.4; 356/364, 369, 937, 630

(56) References Cited

U.S. PATENT DOCUMENTS

| | | | |
|---|---|---|---|
| 4,472,633 A | 9/1984 | Motooka | 250/338 |
| 4,807,994 A | 2/1989 | Felch et al. | 356/326 |
| 5,486,701 A | 1/1996 | Norton et al. | 250/372 |
| 5,625,455 A | * 4/1997 | Nash et al. | 356/369 |
| 5,900,633 A | * 5/1999 | Solomon et al. | 250/339.08 |
| 6,049,220 A | 4/2000 | Borden et al. | 324/765 |

OTHER PUBLICATIONS

"Application of IR Variable Angle Spectroscopic Ellipsometry To The Determination of Free Carrier Concentration Depth Profiler", Tiwald et al., Thin Film Solids, 313–314 (1998).

"PN Junction–Based Wafer Flow Process For Stencil Mask Fabrication" Rangelow et al., J. Vac. Sci. Tech. B. (Nov/Dec) (1998).

* cited by examiner

*Primary Examiner*—Constantine Hannaher
*Assistant Examiner*—Timothy Moran
(74) *Attorney, Agent, or Firm*—James D. Welch

(57) ABSTRACT

Disclosed is spectroscopic ellipsometer system mediated methodology for quantifying thickness and impurity profile defining parameters in mathematical models of impurity profile containing thin membranes having two substantially parallel surfaces which are separated by a thickness, wherein the spectroscopic ellipsometer system operates in near-IR and IR wavelength ranges.

3 Claims, 6 Drawing Sheets

DETERMINATION OF THICKNESS AND IMPURITY PROFILES IN THIN MEMBRANES UTILIZING SPECTORSCOPIC DATA OBTAINED FROM ELLIPSOMETRIC INVESTIGATION OF BOTH FRONT AND BACK SURFACES

This Application is a Continuation-In-Part of Provisional Application Ser. No. 60/183,977 filed Feb. 22, 2000.

TECHNICAL FIELD

The present invention relates to non-destructive characterization of sample systems, and more particularly to spectroscopic ellipsometer system(s) mediated methodology for quantifying thickness and impurity profile defining parameters in mathematical models of impurity profile containing thin membranes comprised of two substantially parallel surfaces which are separated by a thickness, wherein said spectroscopic ellipsometer system(s) operates in near-IR and IR wavelength ranges.

BACKGROUND

In view of developing open stencil lithography mask technology which utilizes open stencil lithography masks formed from thin silicon membranes, (which are typically formed by pn junction stop-etch techniques), a need exists for a non-destructive approach to characterizing thin membrane thickness and impurity profiles in impurity profile containing thin membranes comprised of two substantially parallel surfaces that are separated by a thickness of about 100 microns or less.

A Search of Patents has revealed U.S. Pat. No. 4,472,633 to Motooka which describes use of linearly polarized infrared light to investigate semiconductor wafers. Plots of Ellipsometric PSI vs. Ellipsometric DELTA, as a function of Angle of Incidence and/or Wavelength, for various carrier density profiles and depths are determined. Ellipsometric data obtained from a sample wafer is then utilized to plot Ellipsometric PSI vs. Ellipsometric DELTA, as a function of Angle of Incidence and/or Wavelength, and the results compared to the known plots. Close correlation between sample wafer and a known Ellipsometric PSI vs. Ellipsometric DELTA, as a function of Angle of Incidence and/or Wavelength, is indicative of the sample having a doping profile and depth similar to that of the wafer from which the known Ellipsometric PSI vs. Ellipsometric DELTA data was obtained. Data, is described as obtained utilizing monochromatic light, even though different wavelengths are used in succession where wavelength is the independent variable.

Another U.S. Pat. No. 4,807,994 to Felch et al., describes a non-ellipsometric method of mapping ion implant dose uniformity. Monochromatic Electromagnetic radiation with a bandwidth of not more than 1 nm, (chosen for sensitivity to sample parameters being measured), which has interacted with a sample in Reflectance or Transmission, is monitored by a Spectrophotometer and the results compared to previously obtained similar data regarding film thickness and ion implant doses, and similarities determined.

U.S. Pat. No. 5,900,633 to Solomon et al., describes a non-ellipsometric approach to analyzing patterned samples which involves irradiating a spot which includes first and second pattern regions, measuring eminating radiation, providing known reference spectrum/spectra and comparing measured spectral data thereto to evaluate parameters of layers in said two pattern regions.

U.S. Pat. No. 5,486,701 to Norton et al., describes a non-ellipsometric approach simultaneously utilizing wavelengths in both UV and Visible wavelength ranges to enable calculating a ratio thereof, which in turn is utilized to determine thin film thicknesses.

U.S. Pat. No. 6,049,220 to Borden et al., describes apparatus and method for evaluating semiconductor material. In a major implementation thereof, two beams are caused to illuminate a sample, one having energy above the bandgap and the other having energy near or below the bandgap. The second beam, after interaction with the sample, is monitored and change therein caused by said interaction is indicative of carrier concentration. It is noted that reflectance of an electromagnetic beam from a sample is a function of carrier concentration.

Known relevant art includes Articles, P-N Junction-Based Wafer Flow Process For Stencil Mask Fabrication", Rangelow et al., J. Vac. Sci. Technology B, November/December P. 3592 (1998); and "Application of IR Variable Angle Spectroscopic Ellipsometry To The Determination Of Free Carrier Concentration Depth Profiles", Tiwald et al., Thin Film Solids 313–314, P661, (1998).

In view of known prior art, there remains need for accuracy improving methodology for measuring impurity profiles in substrates, which methodology utilizes electromagnetic radiation with wavelengths in ranges for which the substrate is opaque and transparent, and which method involves utilizing data obtained both when electromagnetic radiation is caused to impinge on one surface, and then the other surface of said substrate.

DISCLOSURE OF THE INVENTION

In a basic sense, the present invention comprises a method of quantifying thickness and impurity profile defining parameters in impurity profile containing thin membranes, comprising providing an impurity profile containing thin membrane, and obtaining ellipsometric data from both first (front) and second (back) sides thereof, in combination with providing a mathematical model of said impurity profile defining parameters which comprises membrane thickness and impurity profile defining parameters, then regressing said mathematical model onto data obtained from both sides of said impurity profile containing thin membrane to evaluate said membrane thickness and impurity profile defining parameters. Note that this can include utilizing data in a procedure selected from the group consisting of:

utilizing the data sets obtained from front and back of the thin membrane simultaneously;

utilizing the data sets obtained from front and back of the thin membrane independently; and utilizing the data sets obtained from front and back of the thin membrane both independently and simultaneously.

The present invention can more accurately be described as a method of quantifying thickness and impurity profile defining parameters in impurity profile containing thin membranes comprised of two substantially parallel surfaces that are separated by a thickness, wherein said method comprises, in any functional order, the steps of:

a. providing an impurity profile containing thin membrane comprised of two substantially parallel surfaces that are separated by a thickness, and providing a spectroscopic ellipsometer system capable of producing spectroscopic data sets at at least one angle of incidence of a beam of electromagnetic radiation to a surface of said impurity profile containing thin membrane when it is mounted in said spectroscopic ellipsometer system;

b. determining a range of wavelengths over which the impurity profile containing thin membrane is essentially transparent and the effect of the presence of said impurity profile has essentially negligible effect;

c. determining a range of wavelengths over which the impurity profile containing thin membrane is essentially transparent, but over which the effect of the presence of said impurity profile has a non-negligible effect;

d. utilizing substantially wavelengths in the range determined in step b., by an approach selected from the group consisting of:
reflection ellipsometry; and
transmission ellipsometry;
obtaining a spectroscopic data set;

e. utilizing substantially wavelengths in the range determined in step c., by reflection ellipsometry as applied to one surface of said impurity profile containing thin membrane, obtaining a spectroscopic data set;

f. utilizing substantially wavelengths in the range determined in step c., by reflection ellipsometry as applied to a surface of said impurity profile containing thin membrane offset from that utilized in step e. by said thickness, obtaining a spectroscopic data set;

g. providing a mathematical model for said impurity profile containing thin membrane including a parameter that quantifies thickness;

h. providing a mathematical model for said impurity profile containing thin membrane including parameters that quantify impurity profile defining parameters;

i. using the spectroscopic data set obtained in step d., regressing the mathematical model provided in step g. thereonto to evaluate the parameter that quantifies thickness;

j. using the thickness arrived at in step i. and the spectroscopic data sets obtained in at least one of the steps e. and f., simultaneously regressing the mathematical model provided in step h. thereonto to evaluate the parameters that quantify the impurity profile.

An alternative embodiment of the present invention method of quantifying thickness and impurity profile defining parameters in impurity profile containing thin membranes which are comprised of two substantially parallel surfaces that are separated by a thickness, can also be recited as comprising, in any functional order, the steps of:

a. providing an impurity profile containing thin membrane comprised of two substantially parallel surfaces that are separated by a thickness, and providing a spectroscopic ellipsometer system capable of producing spectroscopic data sets at at least one angle of incidence of a beam of electromagnetic radiation to a surface of said impurity profile containing thin membrane when it is mounted in said spectroscopic ellipsometer system;

b. determining a range of wavelengths over which the impurity profile containing thin membrane is essentially transparent and the effect of the presence of said impurity profile has essentially negligible effect;

c. determining a range of wavelengths over which the impurity profile containing thin membrane is essentially transparent, but over which the effect of the presence of said impurity profile has a non-negligible effect;

d. utilizing substantially wavelengths in the range determined in step b., by an approach selected from the group consisting of:
reflection ellipsometry; and
transmission ellipsometry;
obtaining a spectroscopic data set;

e. utilizing substantially wavelengths in the range determined in step c., by reflection ellipsometry as applied to one surface of said impurity profile containing thin membrane, obtaining a spectroscopic data set;

f. utilizing substantially wavelengths in the range determined in step c., by reflection ellipsometry as applied to a surface of said impurity profile containing thin membrane offset from that utilized in step e. by said thickness, obtaining a spectroscopic data set;

g. providing a mathematical model for said impurity profile containing thin membrane including parameters that quantify thickness and impurity profile defining parameters;

h. using all obtained spectroscopic data sets, simultaneously regressing the mathematical model thereonto to evaluate the parameters that quantify thickness and the impurity profile defining parameters.

The present invention will be better understood by reference to the Detailed description Section of this Specification, in conjunction with the Drawings.

SUMMARY OF THE INVENTION

It is therefore a purpose and/or objective of the present invention to teach a method of evaluating thickness and impurity profile describing parameters in an impurity profile containing thin film, wherein ellipsometric data is obtained from both sides of the impurity profile containing thin film, and a mathematical model which contains parameters which describe the thickness and impurity profile is then regressed onto data obtained from both said sides of the impurity profile containing thin film, separately and/or simultaneously.

DETAILED DESCRIPTION

The present invention is a spectroscopic ellipsometer system based method which utilizes wavelengths in the near-infrared, (near-IR), (ie. 1–1.7 micron), and infrared (IR), (ie. 2–35 micron), ranges. It is noted that in the near-IR wavelength range, silicon is essentially transparent and impurity, (ie. P-type doping), effects are negligible, but that in the IR wavelength range, while un-doped silicon remains essentially transparent, the "doped" silicon becomes essentially opaque and reflective because of the "metallic" presence of free carriers.

Figure 1:
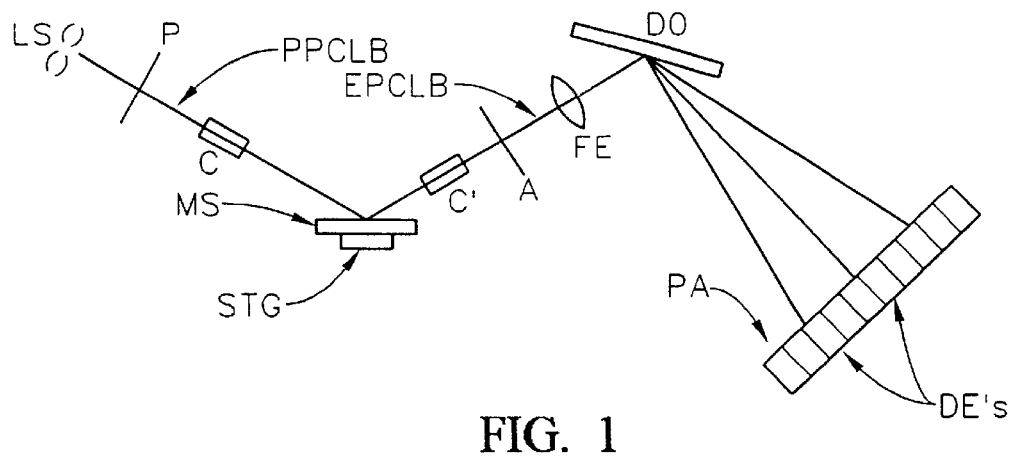
FIG. 1 shows a demonstrative Spectroscopic Ellipsometer System as utilized to obtain data from thin doped membranes as reported in this Specification.

A demonstrative Spectroscopic Ellipsometer System as utilized to obtain data utilized in the present work, is shown in FIG. 1. Note the presence of a Source of Electromagnetic Radiation (LS), a Polarizer (P) for producing a Polarized beam of electromagnetic radiation (PPCLB), a Rotating Compensator (C), Stage (STG) for supporting a Material System (MS), an Analyzer (A), a Dispersive Optics (DO) and a Detector (DET) comprised of a plurality of Detector Elements (DE), each of which is positioned to intercept a different wavelength. Also indicated is Compensator (C') to show that said Rotating Compensator can be placed on either side of the Material System (MS). In most such systems only one (C) or (C') is present, however. Further shown is a Focusing Lens (FE) which can be present to converge an electromagnetic beam (EPCLB) which passes through the Analyzer (A), onto the Dispersive Optics (DO). In use, the Polarizer (P) and Analyzer (A) are typically set to an azimuthal angle and held motionless, and the Compensator (C) or (C') is caused to rotate while an electromagnetic beam (PPCLB) is caused to impinge upon the Material System (MS) such that spectroscopic data is collected by the Detector (DET).

Preferred present invention methodology provides that electromagnetic radiation of near-IR wavelengths be utilized in a spectroscopic ellipsometer system to acquire a reflection or transmission data set which is then applied, via mathematical regression, to evaluate a thickness parameter in a mathematical model of an impurity profile containing thin membrane. Actual experimental results have been acquired utilizing a J.A. Woollam CO. Inc. (M-2000 NIR)tm spectroscopic ellipsometer system configured in a reflection mode, with the angle of incidence of the electromagnetic beam to the investigated surface of the impurity profile containing thin membrane being near the Brewster Angle thereof, in acquiring said data set in this step. See FIG. 2 which shows reflection mode ellipsometric DELTA vs. Wavelength in microns, obtained utilizing an angle of incidence of 75 degrees, for a thin film silicon membrane which was found to be 7.66 microns thick. Note that back-side reflections cause said FIG. 2 data to show interference related effects. In passing, it is noted that the thickness of the impurity profile containing thin membrane is closely related to the spacing between the cyclic peaks in said data, as modified by the refractive index of the silicon. (Note, "E" indicates data obtained while investigating the front of sample and "Er" the Surface near the Doping).

With thickness of said impurity profile containing thin membrane thus determined, the preferred present invention method involves obtaining two reflection mode data sets utilizing electromagnetic radiation of IR wavelengths in a spectroscopic ellipsometer system. One of said reflection mode data sets is obtained with the electromagnetic beam caused to impinge upon one of two substantially parallel surfaces of an impurity profile containing thin membrane, and the second data set is obtained by causing the electromagnetic beam caused to impinge upon the other of said two substantially parallel surfaces. Actual experimental results have been acquired utilizing a J.A. Woollam CO. Inc. (IR-VASE) (Registered Trademark), spectroscopic ellipsometer system configured in a reflection mode, with the angle of incidence of the electromagnetic beam to an investigated surface of the impurity profile containing thin membrane being below the Brewster Angle thereof, (eg. at 68 degrees), while acquiring said data set in this step.

It is noted that where an impurity profile containing thin membrane has the impurities concentrated near one of said two substantially parallel surfaces but removed from the opposite substantially parallel surface, that data obtained with the electromagnetic beam impinging on said opposite surface will produce data which show the results of interference based in the presence of back-side reflections. Where the electromagnetic beam is caused to impinge on the substantially parallel surface near the impurities, acquired data does not demonstrate interference effects, as said impurities cause the silicon to be essentially opaque and reflective of said electromagnetic radiation, thus preventing back-side reflections. FIG. 3 demonstrates actual reflection mode ellipsometric DELTA data obtained utilizing an angle of incidence of 68 degrees to the same impurity profile containing thin membrane that was used to obtain data shown in FIG. 2. Note the onset of Interference prior the wavelength of approximately 3.3 microns, in the data curve obtained when investigating the substantially parallel surface near the impurities, indicating an approach to the case similar to that shown in FIG. 2. While FIG. 2 data was obtained with the near-IR beam impinging on the opposite substantially parallel surface, (ie. the substantially parallel surface removed from the impurities), in the near-IR wavelength range the impurity effects are essentially negligible, hence, backside reflections occur regardless of which substantially parallel surface is investigated. It is also noted that non-parallel surfaces, or uneven thickness, can cause interference effects.

Figure 4:
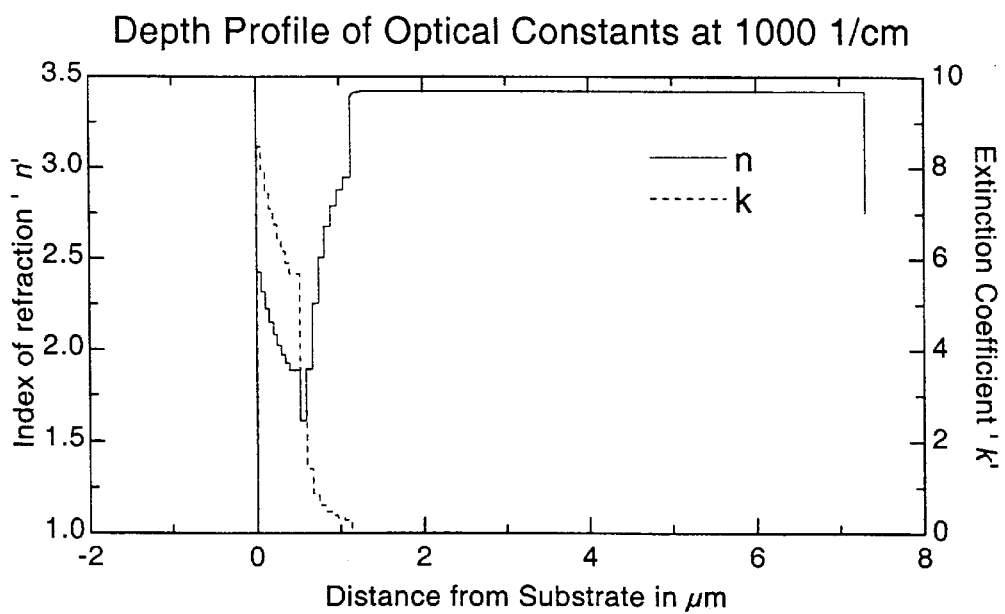
FIG. 4 shows that, for the same thin film membrane used to obtain the data in FIGS. 2 and 3, where IR range wavelengths are utilized, where present, the impurities cause said (n) and (k) to vary, but where said impurities are absent, (k) for instance, quickly becomes essentially zero.
Figure 2:
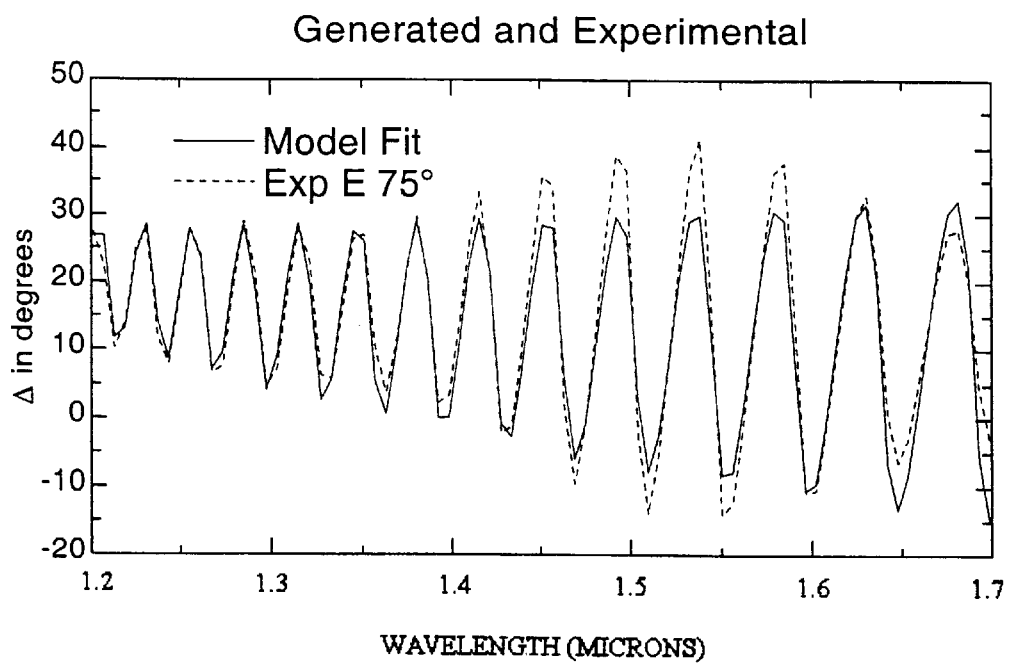
FIG. 2 shows, for a first thin impurity profile containing membrane, reflection mode ellipsometric DELTA vs. Wavelength in microns, obtained utilizing an angle of incidence of 75 degrees, for a thin film silicon membrane which was found to be 7.66 microns thick.
Figure 3:
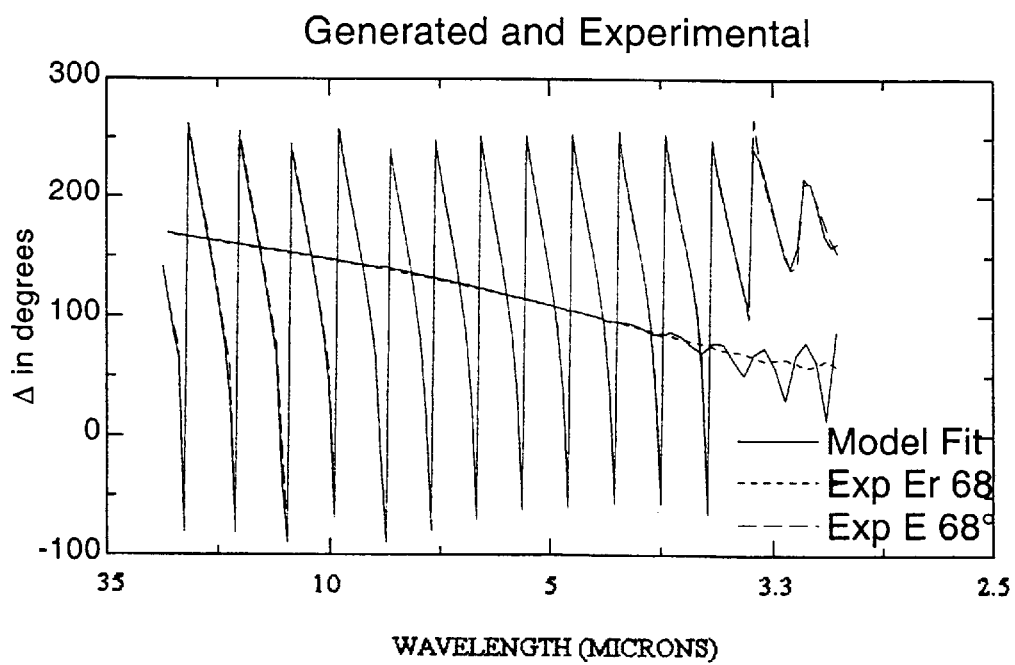
FIG. 3 demonstrates actual reflection mode ellipsometric DELTA data obtained utilizing an angle of incidence of 68 degrees to the same impurity profile containing thin membrane that was used to obtain data shown in FIG. 2.

FIG. 4 shows refractive index (n) and extinction coefficient (k) data for the impurity profile containing thin membrane that was used in providing FIGS. 2 and 3. Note that the location identified as (0) on the "X" axis, is the substantially parallel surface near which is the impurity profile, and the downward vertical line at the right indicates the opposite surface. FIG. 4 shows that where IR range wavelengths are utilized, where present, the impurities cause said (n) and (k) to vary, but where said impurities are absent, (k) for instance, quickly becomes essentially zero.

In the work which produced the foregoing results, the refractive index was modeled in the near-IR with as a Cauchy-dispersion with a Urbach absorption tail. The doping effects in the IR wavelength range were modeled by a Drude model as described in the previously referenced Tiwald et al. article.

It is to be understood that while initial work determined impurity profile containing thin membrane thickness in a first regression utilizing near-IR wavelength range data, and used a second regression based upon two data sets based on IR wavelength range data, it is within the scope of the present invention to obtain all described near-IR and IR wavelength range data and simultaneously regress thereonto to simultaneously evaluate mathematical model thickness and impurity profile describing parameters.

As additional insight, it is mentioned that if an impurity profile containing thin membrane has the impurities concentrated centrally therewithin, data obtained by investigation of either of said two substantially parallel surfaces with a spectroscopic ellipsometer system configured in a reflection mode, and using IR range wavelengths in a beam of electromagnetic radiation caused to impinge thereupon, (eg. at below the Brewster Angle), will show interference effects.

Table 1 summarizes actual experimentally arrived-at results for the impurity profile containing thin membrane investigation of which provided data shown in FIGS. 2–4.

TABLE 1

| | |
|---|---|
| NATIVE OXIDE THICKNESS (TOP) | 0.002 MICRON |
| SILICON DEPLETION REGION | 6.0383 MICRON |
| GRADED SILICON FREE CARRIERS | 1.2517 MICRON |
| NATIVE OXIDE THICKNESS (BOTTOM) | 0.0061 MICRON |

While the above described FIGS. 2–4 provide example to the basic application of the present invention methodology, additional thin membranes have also been investigated by similar techniques, but wherein data was obtained at multiple Angles-of-Incidence, such as 60, 65, and 70 degrees with respect to the thin membrane surfaces. All data was then utilized in regression evaluation of Thin Membrane related parameters.

FIGS. 5–12 show various data for one such additional Thin Membrane system which is characterized as in Table 2:

TABLE 2

| | |
|---|---|
| THERMAL OXIDE | 0.0 MICRON |
| SILICON DEPLETION | 3.1199 MICRON |
| GRADED P-TYPE FREE CARRIER | 1.6882 MICRON |
| P-TYPE FREE CARRIER | 0.0 MICRON |
| THERMAL OXIDE | 0.0010637 MICRON |
| VOID | 1.0 MICRON |

Figure 5:
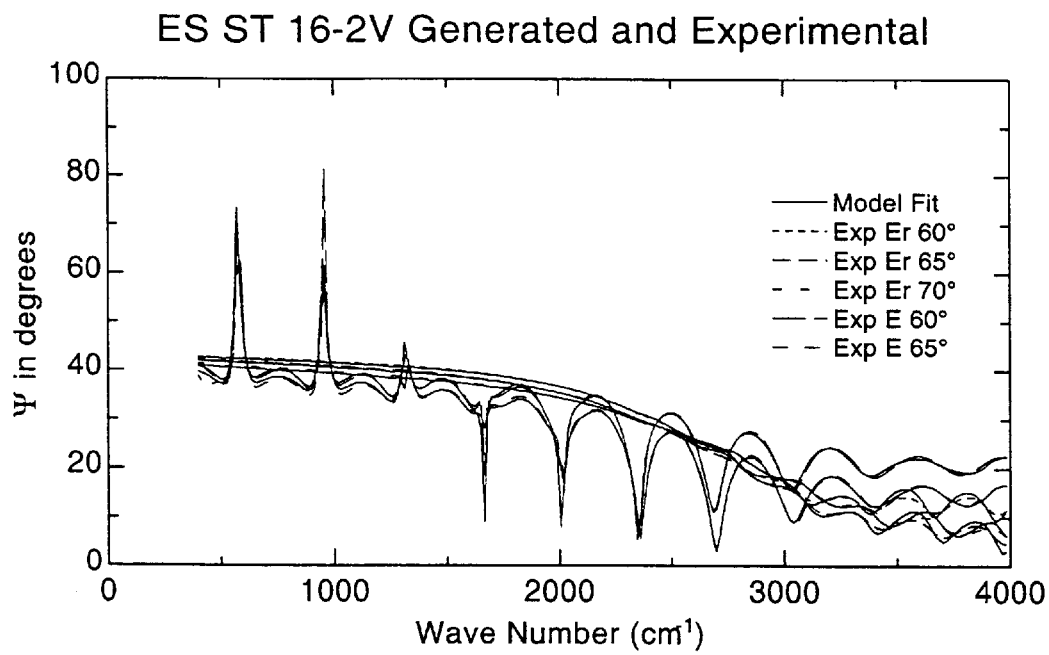
FIGS. 5 and 6 show PSI and DELTA vs. Wave Number, (where Wavelength in Microns is obtained by dividing 10,000 by the Wave Number), for a second impurity profile containing thin film sample.
Figure 6:
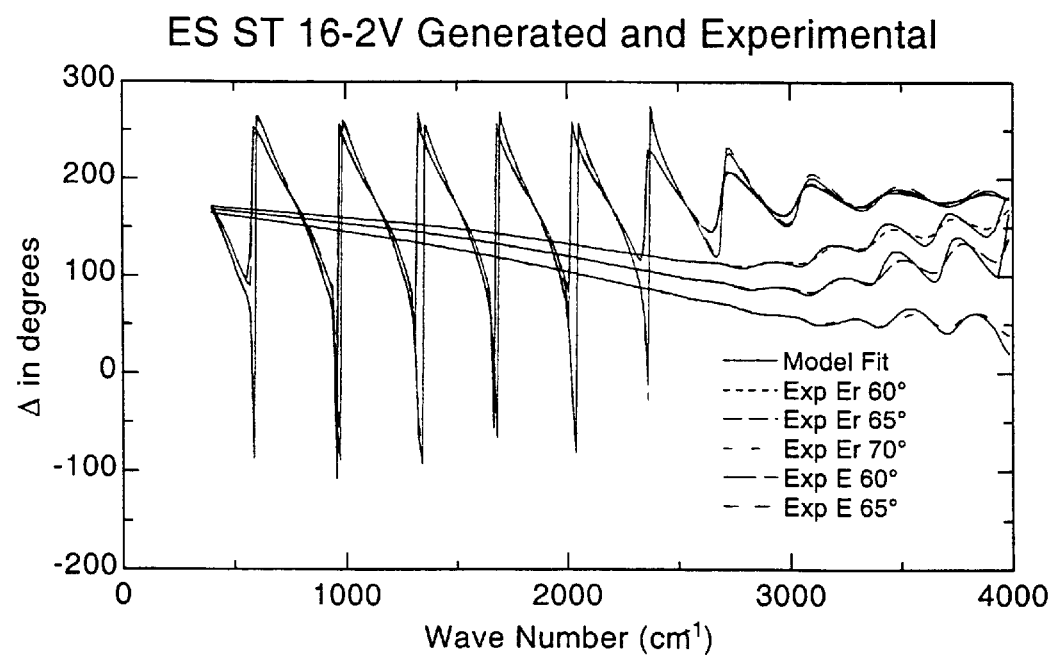
Figure 7:
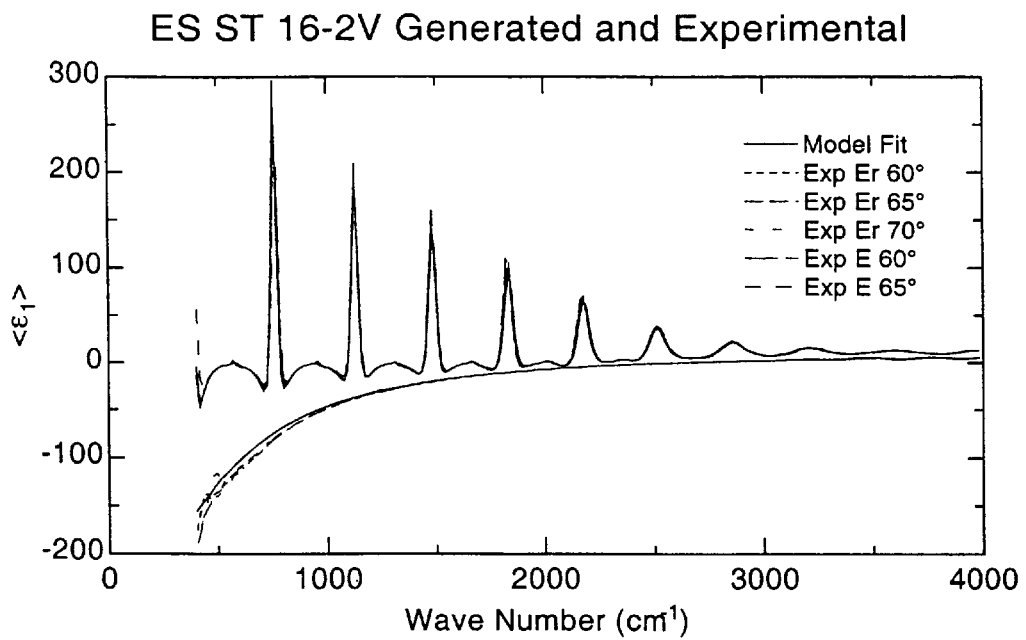
FIGS. 7 and 8 show Psuedo Dielectric Functions for said second thin film sample.
Figure 8:
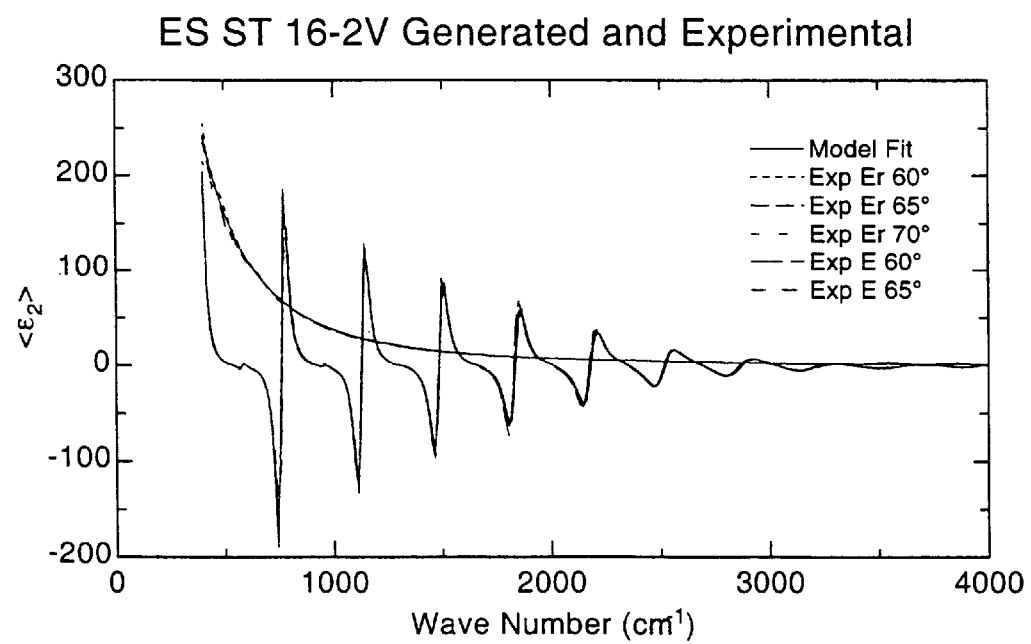
Figure 9:
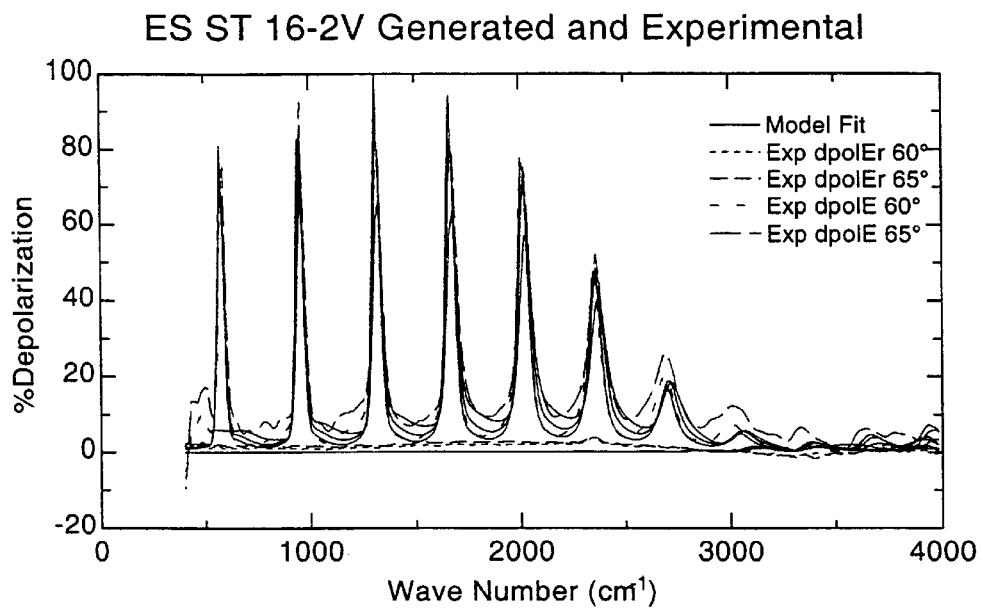
FIG. 9 shows (%) Depolarization for said second thin film sample.
Figure 12:
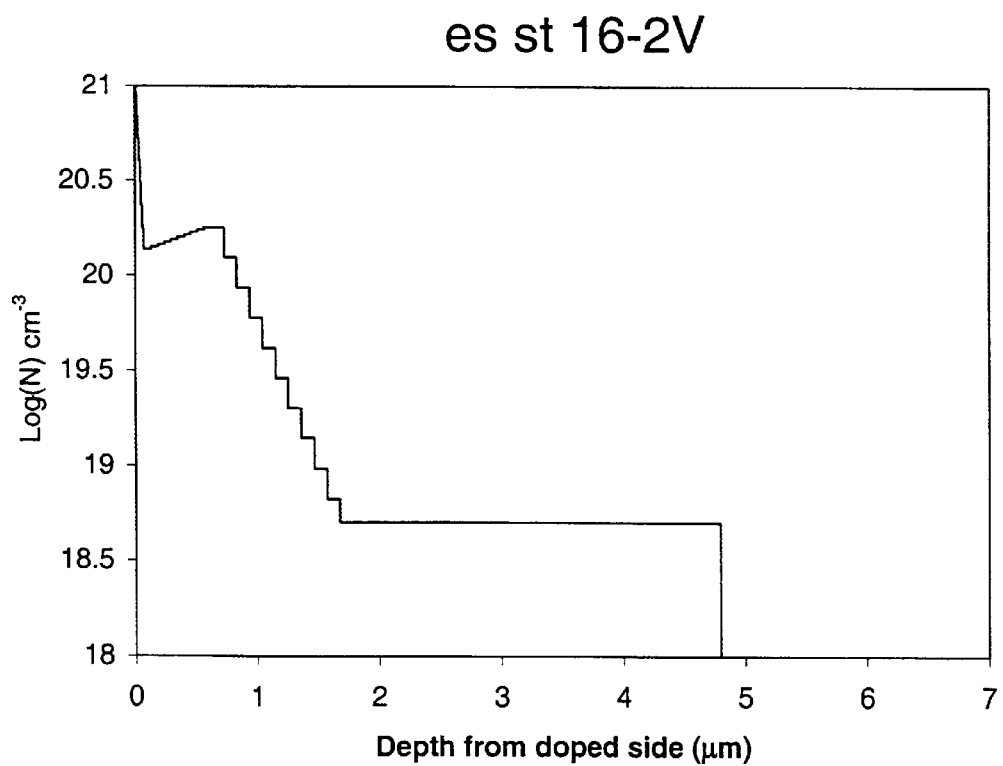
FIG. 12 shows a Log (N) vs. Microns from the Doped Surface of the Thin Membrane for said second thin film sample.
Figure 10:
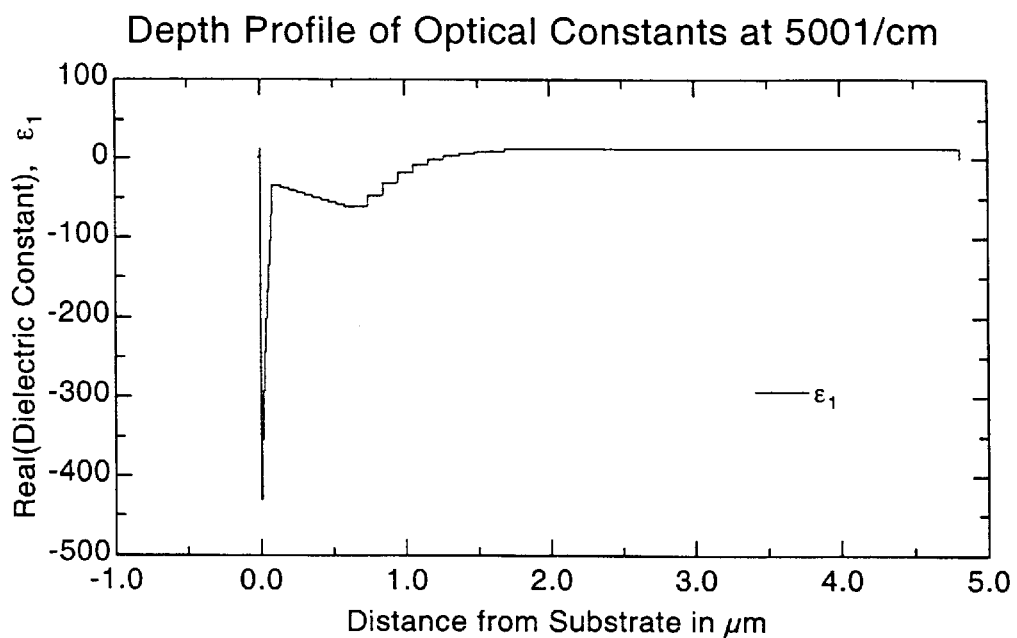
FIGS. 10 and 11 show Real and Imaginary Dielectric Constants as a function of depth into the thin membrane, wherein 0.0 is the surface thereof near the Doping profile for said second thin film sample.
Figure 11:
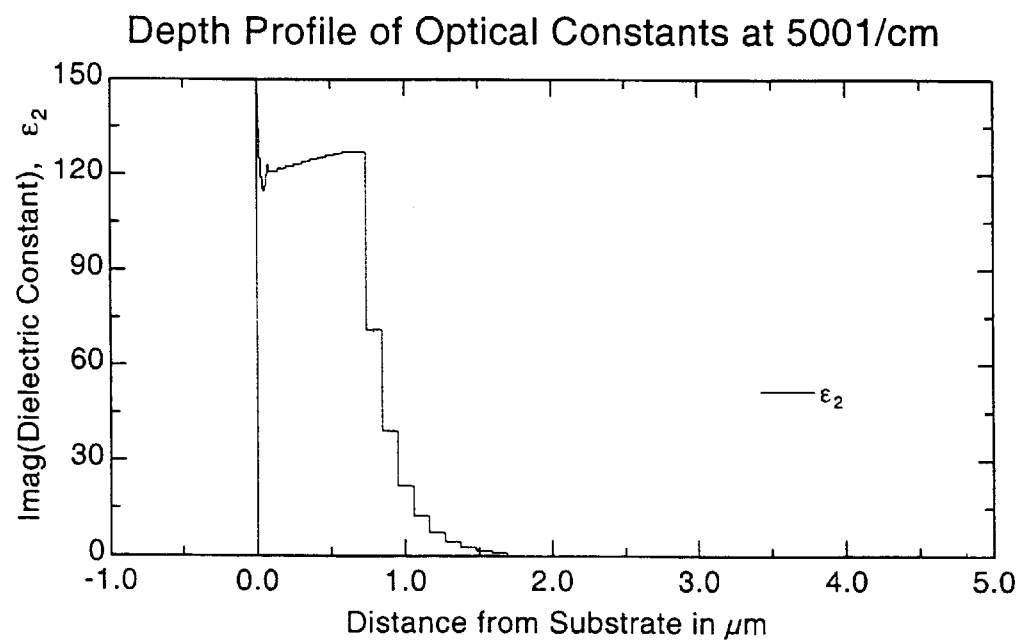

Note in said Figures, "E" indicates data obtained while investigating the front of sample, and "Er" the Surface near the Doping. FIGS. 5 and 6 show PSI and DELTA vs. Wave Number, (where Wavelength in Microns is obtained by dividing 10,000 by the Wave Number). FIGS. 7 and 8 show Psuedo Dielectric Functions. FIG. 9 shows (%) Depolarization, (where (%) Depolarization is a measure of how much $COS^2$ (DELTA)+$SIN^2$(DELTA) deviates from 1.0). FIGS. 10 and 11 show Real and Imaginary Dielectric Constants as a function of depth into the thin membrane, (wherein 0.0 is the surface thereof near the impurity profile). Finally FIG. 12 shows a Log (N) vs. Microns from the Doped Surface of the Thin Membrane, where (N) is concentration per centimeter cubed.

It is to be understood that the terminology "two substantially parallel surfaces that are separated by a thickness" can identify impurity profile containing thin membranes which are not strictly comprised of two precisely parallel surfaces separated by a strictly unvarying thickness, but that said terminology serves to identify a material system which is primarily comprised of two surfaces which have areas defined by effective length and width dimensions which are significantly greater than a thickness separating them.

Additionally, the terminology, "a range of wavelengths over which the impurity profile containing thin membrane is essentially transparent, but over which the effect of the presence of said impurity profile has a non-negligible effect", does not strictly exclude all wavelengths at which an impurity profile is somewhat transparent, but only serves to identify a range of wavelengths over which a beam of electromagnetic radiation comprised thereof substantially reflects from said impurity profile.

It is mentioned that both the (IR-VASE) (Registered Trademark), and the (M-2000 NIR)tm spectroscopic ellipsometer systems are of Rotating Compensator design, hence both are able to measure DELTA values at zero (0.0) degrees.

Finally, while Rotating Compensator Ellipsometer Systems were used as examples in this Specification, any Ellipsometer System which can provide the necessary data are to be considered within the scope of the Claims.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of quantifying thickness and impurity profile defining parameters in impurity profile containing membranes, comprising the steps of providing an ellipsometer system, and sequentially or simultaneosly obtaining ellipsometric data sets from both first and second sides of an impurity profile containing membrane, and providing a mathematical model of said impurity profile defining parameters comprising membrane thickness and impurity profile defining parameters, then performing a mathematical regression of said mathematical model onto data obtained from said impurity profile containing membrane by a selection from the group consisting of:

utilizing the data sets obtained from front and back of the thin membrane simultaneously;

utilizing the data sets obtained from front and back of the thin membrane independently; and utilizing the data sets obtained from front and back of the thin membrane both independently and simultaneously.

to evaluate said membrane thickness and impurity profile defining parameters.

2. A method of quantifying thickness and impurity profile defining parameters in impurity profile containing membranes comprised of two substantially parallel surfaces that are separated by a thickness, said method comprising the steps of:

a. providing an impurity profile containing membrane comprised of two substantially parallel surfaces that are separated by a thickness, and providing a spectroscopic ellipsometer system capable of producing spectroscopic data sets at at least one angle of incidence of a beam of electromagnetic radiation to a surface of said impurity profile containing membrane when it is mounted in said spectroscopic ellipsometer system;

practicing steps b. and c. in either order:

b. determining a range of wavelengths over which the impurity profile containing membrane is essentially transparent and the effect of the presence of said impurity profile has essentially negligible effect;

c. determining a range of wavelengths over which the impurity profile containing membrane is essentially transparent, but over which the effect of the presence of said impurity profile has a non-negligible effect;

practicing steps d., e. and f. in any order, including the possibility of performing two or more steps simultaneously:

d. utilizing substantially wavelengths in the range determined in step b., by an approach selected from the group consisting of:

reflection ellipsometry; and transmission ellipsometry;

obtaining a spectroscopic data set;

e. utilizing wavelengths in the range determined in step c., by reflection ellipsometry as applied to one surface of said impurity profile containing membrane, obtaining a spectroscopic data set;

f. utilizing wavelengths in the range determined in step c., by reflection ellipsometry as applied to a surface of said impurity profile containing membrane offset from that utilized in step e. by said thickness, obtaining a spectroscopic data set;

in conjunction with the foregoing steps, practicing steps g. and h. in either order:

g. providing a mathematical model for said impurity profile containing membrane including a parameter that quantifies thickness;

h. providing a mathematical model for said impurity profile containing membrane including parameters that quantify impurity profile defining parameters;

i. using the spectroscopic data set obtained in step d., performing a mathematical regression of the mathematical model provided in step g. thereonto to evaluate the parameter that quantifies thickness;

j. using the thickness arrived at in step i. and the spectroscopic data sets obtained in at least one of the steps e. and f., simultaneously performing a mathematical regression of the mathematical model provided in step h. thereonto to evaluate the parameters that quantify the impurity profile.

3. A method of quantifying thickness and impurity profile defining parameters in impurity profile containing membranes comprised of two substantially parallel surfaces that are separated by a thickness, said method comprising the steps of:

a. providing an impurity profile containing membrane comprised of two substantially parallel surfaces that are separated by a thickness, and providing a spectroscopic ellipsometer system capable of producing spectroscopic data sets at at least one angle of incidence of a beam of electromagnetic radiation to a surface of said impurity profile containing membrane when it is mounted in said spectroscopic ellipsometer system;

practicing steps b. and c. in either order:

b. determining a range of wavelengths over which the impurity profile containing membrane is essentially transparent and the effect of the presence of said impurity profile has essentially negligible effect;

c. determining a range of wavelengths over which the impurity profile containing membrane is essentially transparent, but over which the effect of the presence of said impurity profile has a non-negligible effect;

practicing steps d., e. and f. in any order, including the possibility of performing two or more steps simultaneously:

d. utilizing substantially wavelengths in the range determined in step b., by an approach selected from the group consisting of:
  reflection ellipsometry; and
  transmission ellipsometry;
obtaining a spectroscopic data set;

e. utilizing substantially wavelengths in the range determined in step c., by reflection ellipsometry as applied to one surface of said impurity profile containing thin membrane, obtaining a spectroscopic data set;

f. utilizing substantially wavelengths in the range determined in step c., by reflection ellipsometry as applied to a surface of said impurity profile containing membrane offset from that utilized in step e. by said thickness, obtaining a spectroscopic data set;

g. in conjunction with the foregoing steps providing a mathematical model for said impurity profile containing membrane including parameters that quantify thickness and impurity profile defining parameters;

h. using all obtained spectroscopic data sets, simultaneously performing mathematical regression of the mathematical model thereonto to evaluate the parameters that quantify thickness and the impurity profile defining parameters.

* * * * *